(12) United States Patent
Hillman et al.

(10) Patent No.: US 9,891,209 B2
(45) Date of Patent: Feb. 13, 2018

(54) ELECTRODE ASSEMBLY FOR MEASUREMENT OF PLATELET FUNCTION IN WHOLE BLOOD

(71) Applicant: CA Casyso GmbH, Basel (CH)

(72) Inventors: Robert Hillman, San Diego, CA (US); Michael M. Gorin, Incline Village, NV (US); Cory Lee McCluskey, Encinitas, CA (US)

(73) Assignee: C A Casyso GmbH (CH)

( * ) Notice: Subject to any disclaimer, the term of this patent is extended or adjusted under 35 U.S.C. 154(b) by 160 days.

(21) Appl. No.: 14/864,634

(22) Filed: Sep. 24, 2015

(65) Prior Publication Data

US 2016/0349234 A1    Dec. 1, 2016

Related U.S. Application Data

(60) Provisional application No. 62/168,717, filed on May 29, 2015.

(51) Int. Cl.
```
G01N 27/02      (2006.01)
G01N 33/487     (2006.01)
G01N 27/07      (2006.01)
```
(52) U.S. Cl.
CPC ....... *G01N 33/48707* (2013.01); *G01N 27/07* (2013.01)

(58) Field of Classification Search
CPC .................. G01N 33/48707; G01N 27/07
USPC .......................... 324/443, 448, 691
See application file for complete search history.

(56) References Cited

U.S. PATENT DOCUMENTS

| | | | |
|---|---|---|---|
| 7,901,629 B2 * | 3/2011 | Calatzis | G01N 27/07 422/536 |
| 7,951,606 B2 | 5/2011 | Pei et al. | |
| 8,003,401 B2 | 8/2011 | Tonnessen et al. | |
| 2013/0270113 A1 | 10/2013 | Huang | |
| 2015/0253271 A1 * | 9/2015 | Giridhar | G01N 27/07 702/53 |

OTHER PUBLICATIONS

PCT International Search Report and Written Opinion, PCT Application No. PCT/US16/34501, dated Aug. 31, 2016, 17 pages.
International Preliminary Report on Patentability and Written Opinion, International Application No. PCT/US2016/034501, dated Dec. 14, 2017, 9 pages.

* cited by examiner

*Primary Examiner* — Farhana Hoque
(74) *Attorney, Agent, or Firm* — Burns & Levinson LLP

(57) ABSTRACT

A platelet impedance measurement system including an electrode assembly allows for measurement of platelet function in blood. The assembly includes a substrate that acts as a substantially rigid base and includes an electrode. A portion of the electrode is exposed such that, when the electrode is placed in blood, the exposed portion is in contact with the blood for measuring impedance changes as platelets adhere to the electrode. Wires of the electrode can be attached to each end of the substrate and can run within a groove along a portion of the substrate. The substrate includes an open area where the wires in the groove exit and re-enter the substrate at the end of the substrate, allowing the wires to be exposed to the blood. The open area includes a brace, ensuring that the exposed wires are held in the appropriate placement relative to each other and to the cuvette.

27 Claims, 12 Drawing Sheets

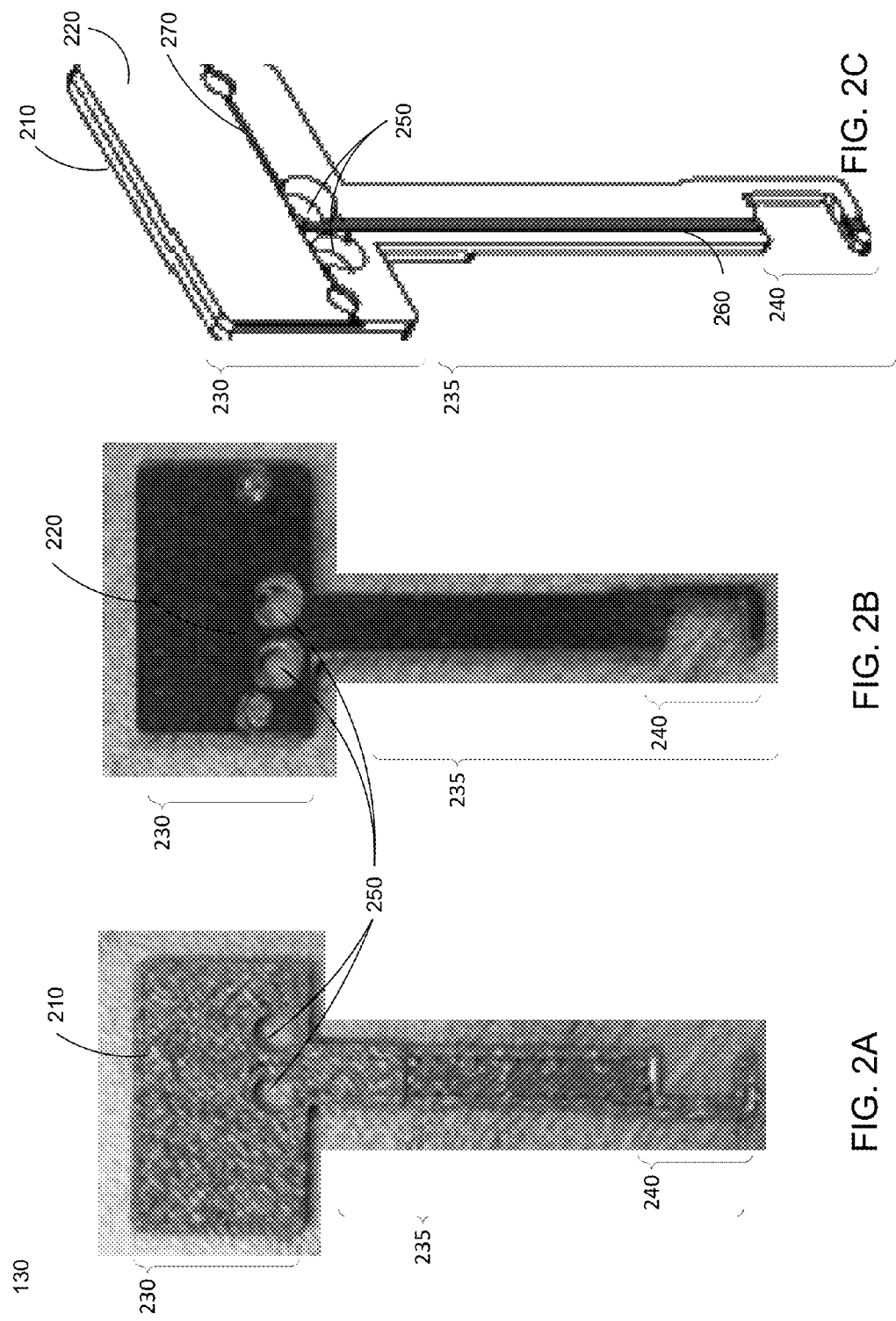

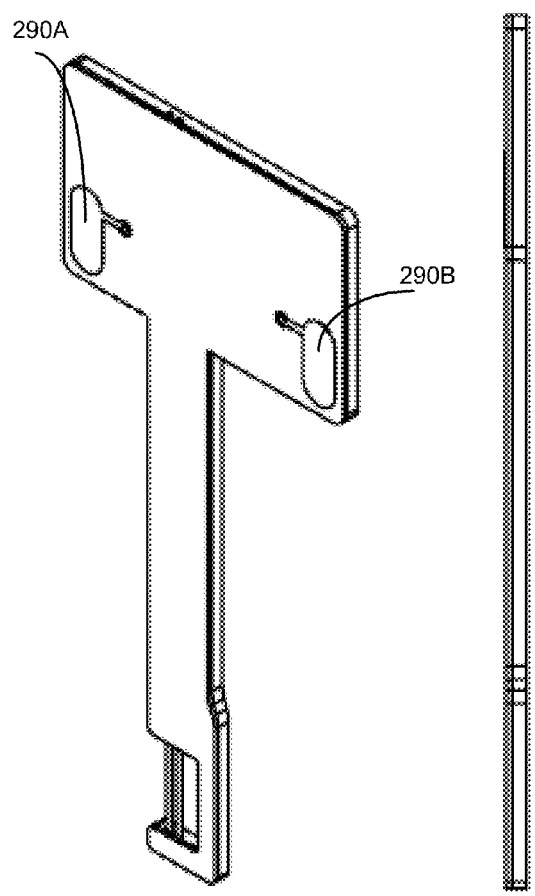 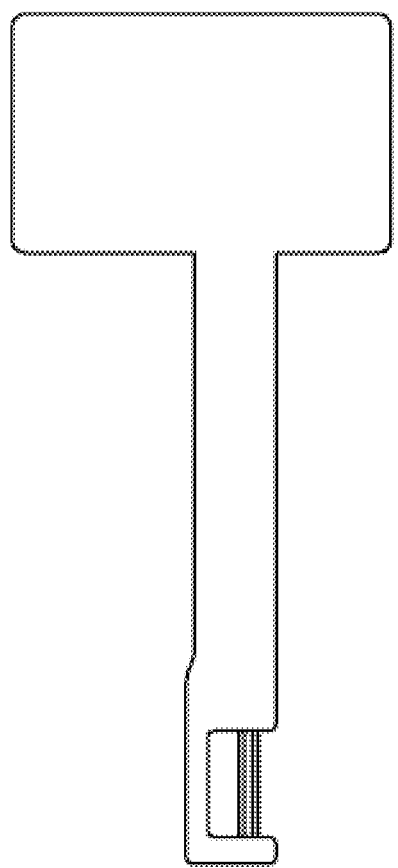
FIG. 2H     FIG. 2I     FIG. 2J

US 9,891,209 B2

ELECTRODE ASSEMBLY FOR MEASUREMENT OF PLATELET FUNCTION IN WHOLE BLOOD

CROSS-REFERENCE

This application claims the benefit of U.S. Provisional Application No. 62/168,717, filed May 29, 2015, which is incorporated by reference in its entirety.

BACKGROUND

This invention relates generally to devices for taking measurements in blood, such as measuring platelet function or aggregation, and more specifically to an electrode assembly used in the devices for measuring platelet function or aggregation.

Platelets are a type of blood cell that plays a role in wound healing. There are various stages during healing of an injury, including hemostasis (i.e., blood clotting), during which platelets in the blood attach to or aggregate at the site of the injury. For example, the attached platelets undergo various changes to stimulate clotting, including changing into a different shape and releasing chemical signals promoting clotting. Given these known normal responses for platelets to various aggregating reagents, responses of platelets in blood to those aggregating reagents can be tested and observed to reveal disorders, dysfunction, and normalcy of a person's platelet function. One method for testing platelet aggregation is the impedance method, or impedance aggregometry method, where platelets in anti-coagulated blood are held and stirred at a specific temperature of 37° C. in a cuvette or other suitable container that includes an electrode. Impedance measurements between two wires of the electrode are taken for various mixtures of the platelets and aggregating reagents. Conventional devices set up for the impedance method include an electrode assembly that can be placed in the cuvette including the platelets, but conventional electrode assemblies have various limitations. For example, the conventional electrode assemblies include flexible, non-rigid substrates along with wires that are minimally anchored, and hence do not allow for consistent reproducibility of placement of the wires relative to each other on the electrode assemblies and relative to the cuvette in which the electrode assembly is placed for measurement. In addition, the signal to noise ratio for conventional electrode assemblies is mediocre. Conventional assemblies can also be difficult to manufacture.

SUMMARY

A platelet impedance measurement system including an electrode assembly for measurement of platelet function in whole blood is disclosed herein. The system includes a container, a mixer (e.g., a stir bar), an electrode assembly, and an electrode. The container is large enough (e.g., larger than a threshold size), or has an opening large enough (e.g., larger than a threshold cross-sectional area), to encompass a portion of the electrode assembly, such as the electrode portion, and to hold a suitable sample, such as whole blood for impedance measurements. The system can also include one or more connections at which the electrode assembly couples with the container. For example, a substrate of the electrode assembly can include slots or tabs on either side of the substrate that couple to, connect to, or rest on an edge of the container. The electrode assembly includes the substrate, which acts as a substantially rigid base, and the electrode, which can include two wires. A portion of the electrode is exposed such that, when the electrode is placed in the sample (e.g., whole blood) held in the container, the exposed portion is in contact with the sample for measuring impedance changes as platelets adhere to the electrode. The wires can be attached to each end of the substrate and can run within a groove along a portion of the substrate, which can include an open area where the wires in the groove exit and then re-enter the substrate at the end of the substrate, allowing the wires to be exposed to the sample. The open area can include a brace, ensuring that the exposed wires are held in the appropriate placement relative to each other and relative to the cuvette.

BRIEF DESCRIPTION OF THE DRAWINGS

FIG. 2A illustrates a first layer of a substrate of an electrode assembly for measurement of platelet function in whole blood, in accordance with an embodiment.

FIG. 2B illustrates a second layer of a substrate of an electrode assembly for measurement of platelet function in whole blood, in accordance with an embodiment.

FIG. 2C illustrates a substrate assembly of an electrode assembly for measurement of platelet function in whole blood, in accordance with an embodiment.

FIG. 2H illustrates a front perspective view of an electrode assembly having a single layer substrate, in accordance with an embodiment.

FIG. 2I illustrates a side view of an electrode assembly having a single layer substrate, in accordance with an embodiment.

FIG. 2J illustrates a back view of an electrode assembly having a single layer substrate, in accordance with an embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Overview

Figure 1:
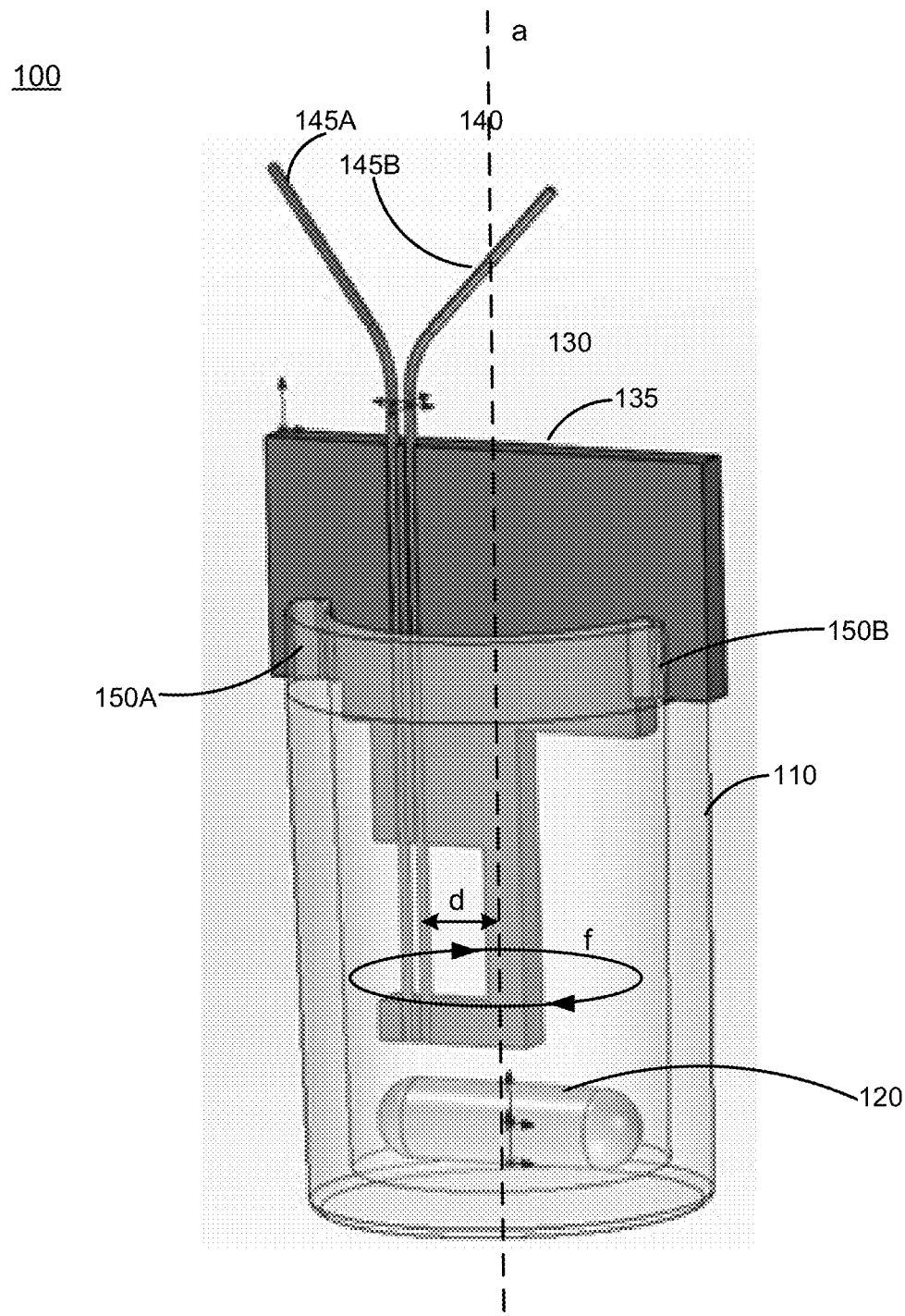
FIG. 1 is a system environment for use with an electrode assembly for measurement of platelet function in whole blood, in accordance with an embodiment.

FIG. 1 is a platelet impedance measurement system 100 for use with an electrode assembly 130 for measurement of platelet function in whole blood. The system 100 includes a container 110, a mixer 120, an electrode assembly 130, and an electrode 140. FIG. 1 illustrates an experimental design in which the wires 145A and 145B are shown free, but in a commercial design, the wires 145A and 145B can be contained within the electrode assembly 130, as is shown in later figures. FIG. 1 shows one embodiment of an electrode assembly 130 design, and the remaining figures show other embodiments of the electrode assembly 130 design. In one embodiment, the container 110 is a cuvette, test tube, a flask, a microtiter plate, or other suitable sample holder or container that is large enough (e.g., larger than a threshold size) or has a diameter, opening, or cross-sectional area larger than a threshold cross-sectional area to encompass a cross-sectional area of a portion of the electrode assembly 130, such as the electrode 140, and hold the whole blood, saline, one or more reagents, any other suitable sample, and any combination thereof for impedance measurements. For example, the sample can include 50% whole blood, 50% saline, and 20 µL of reagent. In one embodiment, the container 110 holds 300 µL or 400 µL of sample but can hold 200 µL to 600 µL of sample and be transparent, slightly transparent, or have a suitable viewing window so the sample within the container 110 is visible to a user of the container 110. The mixer 120 can be a stir bar, rotor, or other suitable rotating part that mixes or stirs the sample in the container 110. The wires are positioned off-center in the container 110 (such as the cuvette) relative to a center vertical axis "a" of the container 110, such that the wires are positioned perpendicular to a flow "f" of the blood moving around the inside of the container. The blood can flow around the internal circumference of a cuvette container. Distance "d" is the distance between the wires and the central vertical axis a of the container 110.

The system 100 can also include one or more connections, such as 150A and 150B, at which the electrode assembly 130 connects or couples with the container 110. For example, a substrate 135 of the electrode assembly 130 can include slots or tabs on either side of the substrate 135 that couple to, connect to or rest on an edge of the container 110, such as the design shown in FIG. 1. Other attachment designs can also be used (e.g., a snapping or locking feature that snaps or couples the electrode assembly 130 to the edge of the container 110). The electrode assembly 130 includes the substrate 135, acting as a substantially rigid base, and the electrode 140, which comprises two wires 145A and 145B or any other suitable connection that can bear electricity, as further described below in conjunction with FIG. 2.

Electrode Assembly

FIGS. 2A and 2B illustrate another embodiment of the electrode assembly 130 having a different shape than the design shown in FIG. 1. FIGS. 2A and 2B show the substrate 135 of the electrode assembly 130 without the wires 145A and 145B. Specifically, FIGS. 2A and 2B illustrate a first layer 210 and a second layer 220, respectively, of a substrate 135 of an electrode assembly 130 for measurement of platelet function in whole blood. FIG. 2C illustrates a substrate 135 assembly of an electrode assembly 130 for measurement of platelet function in whole blood where the first layer 210 and the second layer 220 of the substrate 135 are joined in the electrode assembly 130. Thus, the substrate 135 of the electrode assembly 130 acts as a substantially rigid base and can include a plurality of layers (e.g., a first layer 210 and a second layer 220) that combine to form the substantially rigid base or can be a single layer (see FIGS. 2H-2J). The substrate 135 can be composed of a rigid plastic or other similar material.

A top portion 230 of the electrode assembly 130 can act as a portion that rests on, couples to, or attaches to the container 110 such as a cuvette or otherwise stabilizes the assembly 130 relative to the container 110 during measurement of the blood sample. This top portion 230 has a greater width than the width or thickness of the bottom portion 235 or arm that makes up the rest of the electrode assembly 130 such as along the rest of the electrode assembly 130 below the top portion 230 (hereon the bottom portion 235). In one embodiment, the electrode assembly 130 is 3 to 3.5 cm long from the top of the top portion 230 to the bottom of the bottom portion 235. In one embodiment, the top portion 230 by itself can be 1.2 to 1.6 cm wide (measuring from left to right in FIG. 2A) and 0.6 to 1.2 cm long (measuring from top to bottom of the top portion 230 by itself) and the bottom portion 235 can be 0.2 to 0.5 cm wide (measuring from left to right) and 1 to 3 cm long (measuring from top to bottom) or any suitable length such that the bottom portion 235 fits into the container 110. Further, the bottom portion 235 is attached to the top portion 230 such that the exposed wires 145A and 145B of the brace 240 at the bottom of the bottom portion 235 are positioned between the center of the container 110 and the edge of the container 110. In another embodiment, a center of the bottom portion of the electrode assembly and a center of the top portion of the electrode assembly are not the same such that the center of the bottom portion is not aligned with the center of the top portion. In other words, the bottom portion is off center relative to the top portion, or is a threshold distance from but parallel to the center of the top portion. Therefore, in the embodiments shown in the Figures, the bottom portion 235 is attached to the top portion 230 at a vertical axis parallel to the exposed portion of the wires 145A and 145B.

Other dimensions can also be used in other designs. For example, the top portion 230 can be wider for placement in different container 110 or cuvette designs that have different widths. Similarly, the bottom portion 235 can have different lengths for use in different containers 110 or cuvettes having different heights. Though not shown in the FIGS. 2A-2C, the top portion 230 can include slots or tabs, or other connectors, for connecting or coupling to the edge of the container 110 or cuvette during use.

Figure 2D:
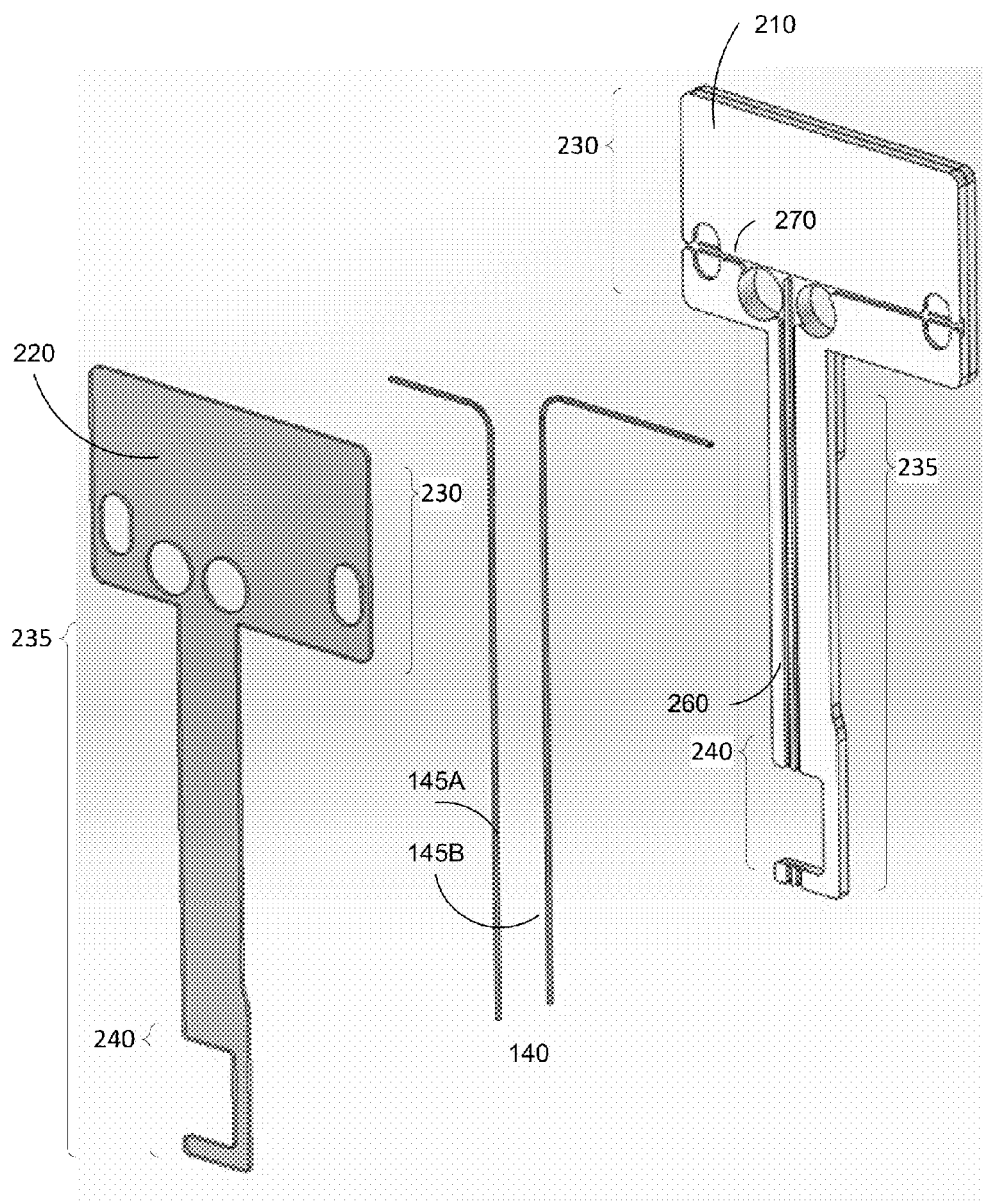
FIG. 2D illustrates components of an electrode assembly including a first layer of a substrate of the electrode assembly, a second layer of the substrate of the electrode assembly, and an electrode including two wires, in accordance with an embodiment.
Figure 2E:
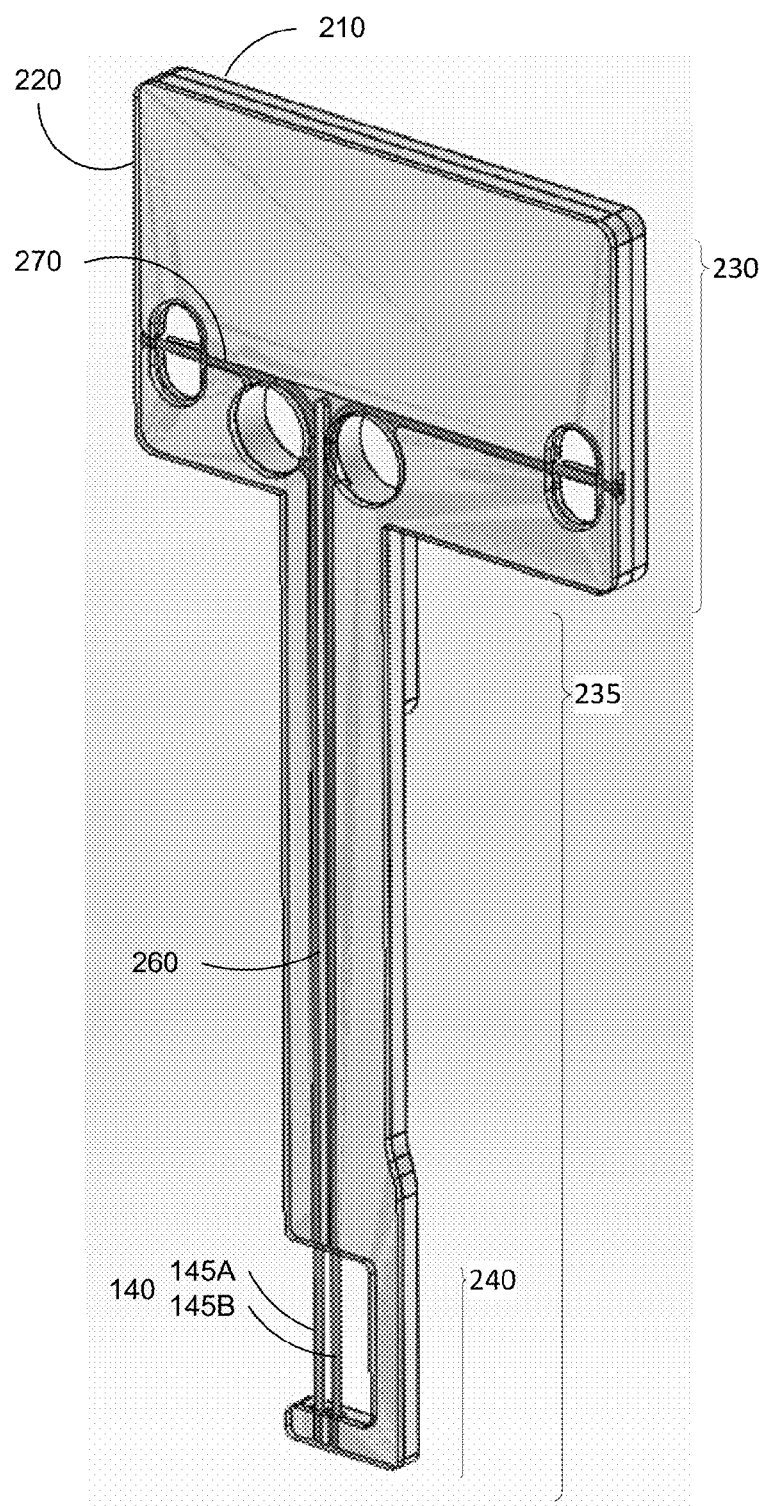
FIG. 2E illustrates a perspective view of assembled components of an electrode assembly including a first layer of a substrate of the electrode assembly, a second layer of the substrate of the electrode assembly, and an electrode including two wires, in accordance with an embodiment.
Figure 2F:
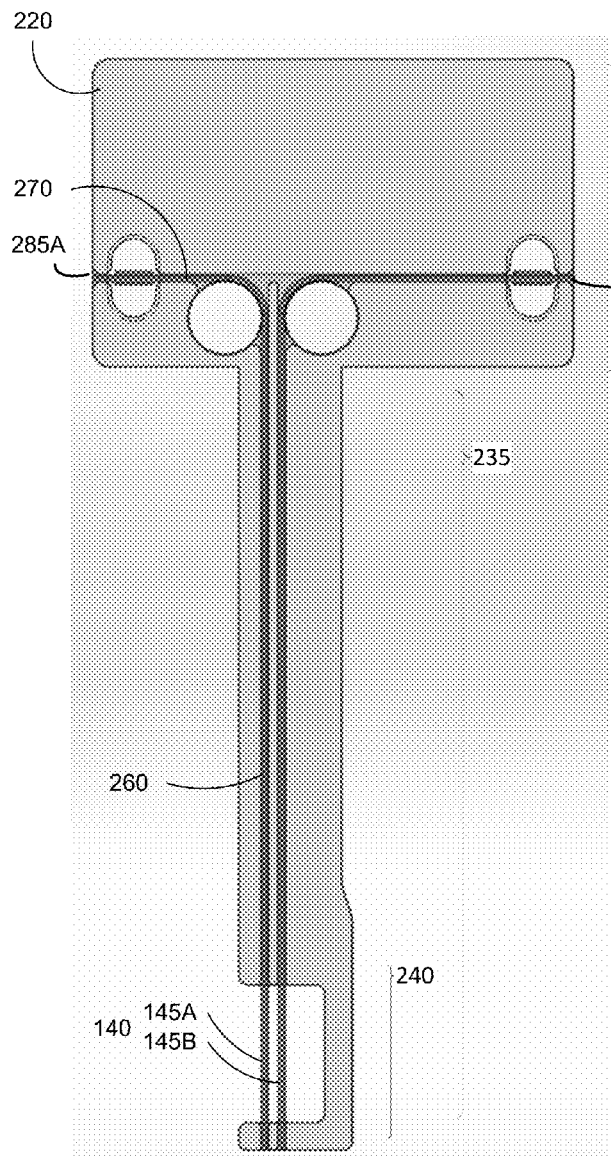
FIG. 2F illustrates a front view of assembled components of an electrode assembly including a first layer of a substrate of the electrode assembly, a second layer of the substrate of the electrode assembly, and an electrode including two wires, in accordance with an embodiment.
Figure 2G:
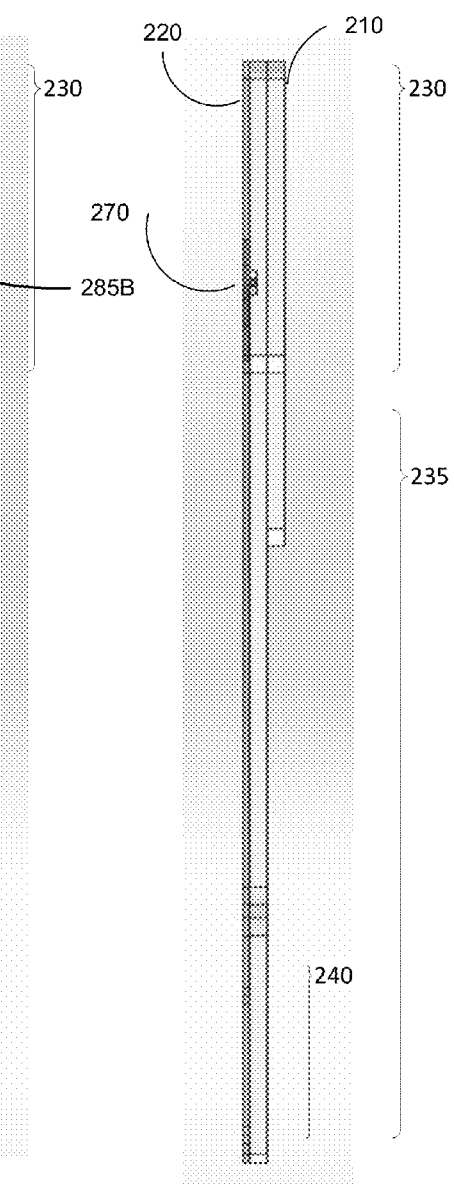
FIG. 2G illustrates a side view of assembled components of an electrode assembly including a first layer of a substrate of the electrode assembly, a second layer of the substrate of the electrode assembly, and an electrode including two wires, in accordance with an embodiment.

As stated previously, the electrode 140 is included in the electrode assembly 130, which can include one or more grooves 260 to guide placement of the wires 145A and 145B of the electrode 140 along the bottom portion 235 of the electrode assembly 130. Alternatively, the grooves 260 can be raised guides or any other suitable indicator to help align the two wires 145A and 145B of the electrode 140. FIG. 2D illustrates the electrode assembly 130 including the first layer 210 of the substrate 135, the second layer 220 of the substrate 135, and the electrode 140 including the two wires 145A and 145B. Specifically, FIG. 2D illustrates how the various components of the electrode assembly 130 are joined together and FIGS. 2E, 2F, and 2G illustrate a perspective view, a top view, and a side view, respectively, of the assembled electrode assembly 130. FIGS. 2H-2J show a single layer electrode design, including a front perspective view, a side view, and a back view, respectively.

As stated previously, the wires 145A and 145B of the electrode 140 are placed on a layer of the substrate 135 (e.g., the first layer 210), along the grooves 260, which may be on the first layer 210, the second layer 220, or both the first and second layers 210 and 220 of the substrate 135. The width of the grooves 260 is wide enough for the wires 145A and 145B of the electrode 140. For example, if there is one large groove 260, then the width of the groove is at least wider than the width of two wires 145A and 145B so that there is a space between the wires 145A and 145B. Alternatively, if there are two grooves 260 for the two wires 145A and 145B, then each of the grooves 260 are at least the width of one of the wires 145A and 145B of the electrode 140. The width or diameter of the wires 145A and 145B can be 0.2 to 0.25 mm or in the range of 0.1 mm to 0.4 mm. In the embodiment where there are two grooves 260, the distance between the two grooves 260 is the same at each point along the bottom portion 235 of the electrode assembly 130, as shown in FIG. 2C, such that the wires 145A and 145B are substantially parallel to each other and spaced a substantially equal distance apart from each other along their lengths. The distance between the two wires 145A and 145B along the length of the bottom portion 235 of the substrate 135 can be 0.25 mm or in the range of 0.1 to 1 mm.

Further, to ensure that the wires 145A and 145B are still the same distance at the base of the bottom portion 235 farthest from the top portion 230, the electrode assembly 130 also has a brace 240 that has an opening to expose a portion of the electrode 140 and the length of the opening in the brace 240 can be 4 mm long or in the range of 2 to 6 mm. Therefore, when the electrode 140 and bottom portion 235 of the electrode assembly 130 are placed in the whole blood (e.g., in the container 110), the exposed portion of the electrode 140 is in contact with the blood and impedance changes of the platelets in the blood can be measured as the platelets adhere or aggregate to the exposed portion of the electrode 140. The portion of the electrode 140 within the substrate 135 can be sealed within the substrate 135 such that only the exposed portion of the electrode 140 contacts the sample in the container 110. The distance of the wires 145A and 145B in the exposed portion of the electrode 140 is kept the same along the wires 145A and 145B due to the grooves 260, as described previously. In other words, the bottom portion 235 of the electrode assembly 130 includes an open area at the brace 240 where the wires 145A and 145B of the electrode 140 in the one or more grooves 260 exit the substrate 135 at the top of the brace 240 exposing the wires 145A and 145B to the blood. Then, the wires 145A and 145B of the electrode 140 re-enter the substrate 135 again at an end of the brace 240 and the brace 240 provides a rigidity to the exposed portion of the wires 145A and 145B. The bottom of the opening of the brace 240 for the exposed portion of the wires 145A and 145B is 2 to 7 mm from the bottom of the container 110 holding the sample.

Figure 3:
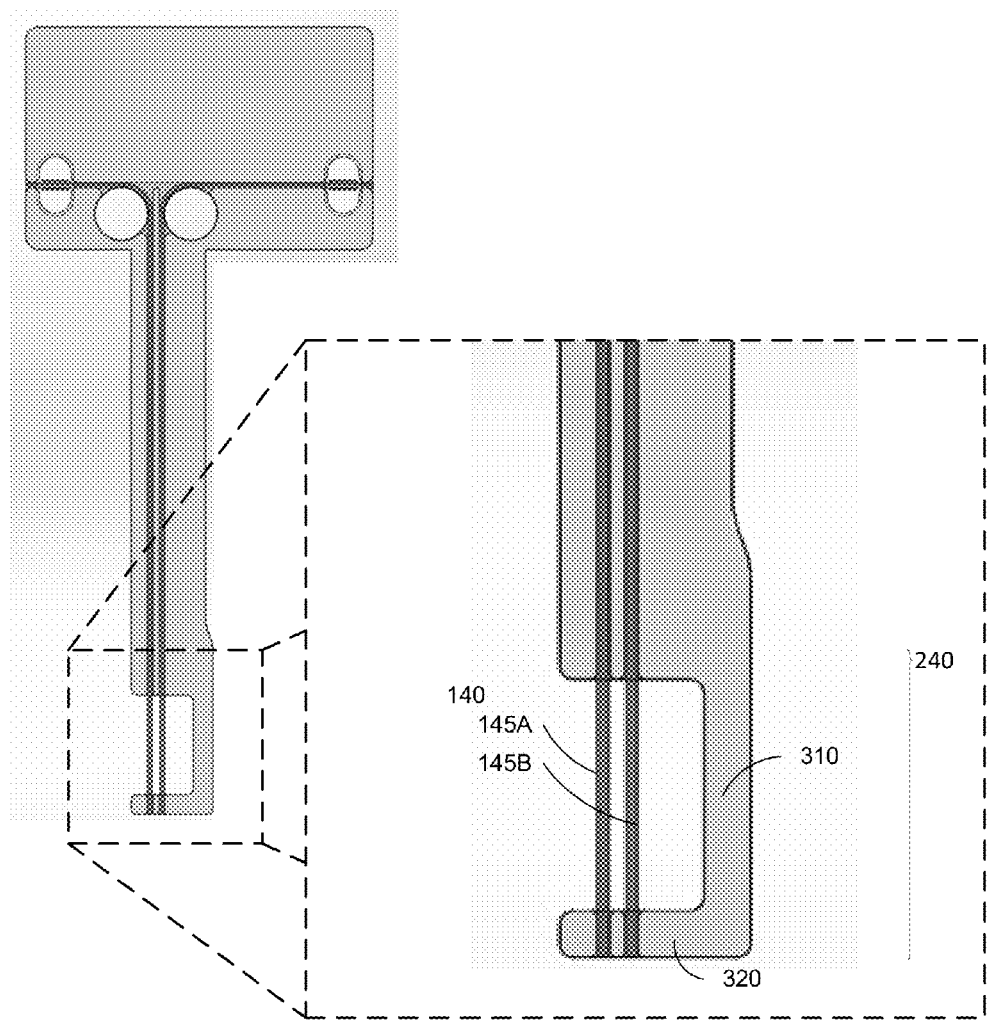
FIG. 3 illustrates components of a brace of an electrode assembly, in accordance with an embodiment.

Describing the brace 240 in more detail in conjunction with FIG. 3, in one embodiment, the brace 240 is a C-shaped, L-shaped, or curved portion that holds and provides rigidity to the exposed wires 145A and 145B in the blood sample held in the container 110. The brace 240 includes a bracing arm 310 that extends vertically away or substantially vertically away from the lowermost part of the bottom portion 235 of the substrate 135, and includes a securing base 320 that extends horizontally away from the bracing arm 310. In alternative embodiments, the bracing arm 310 can extend away in any suitable angle from the lowermost part of the bottom portion 235 as long as the securing base 320 extends substantially horizontally away from the bracing arm 310 and the bottom portion 235 still remains in the container 110. The securing base 320 secures the end of the wires 145A and 145B that exit from the lowermost part of the bottom portion 235 of the substrate 135 such that they then re-enter the substrate 135 at the securing base 320 and are secured within the securing base 320. The bracing arm 310 braces the bottom portion 235 of the substrate 135 to the securing base 320 such that the wires 145A and 145B are secured in a position relative to the substrate 135 and, generally, are not moveable relative to the substrate 135. The bracing arm 310 can be positioned farther from or closer to the wires 145A and 145B than is shown in the Figures. The brace 240 can also have a different length such that more or less of the wires 145A and 145B is exposed and can have a different shape and size. In this manner, the electrode assembly 130 can provide a very reproducible and precise positioning of the wires 145A and 145B relative to one another and relative to the container 110 or cuvette since the wires 145A and 145B are anchored at both the top and the bottom of the exposed region, and the top and bottom of the exposed region are themselves anchored to each other with the bracing arm 310. This anchored design also provides for a better signal-to-noise ratio than conventional designs.

The brace 240 also allows for positioning of the wires 145A and 145B within the cuvette such that the wires 145A and 145B are off-center in the container 110 (such as the cuvette) relative to a center vertical axis "a" of the container 110, such that the wires are positioned perpendicular to a flow "f" of the blood moving around the inside of the container (see FIG. 1). Distance "d" is the distance between the wires and the central vertical axis a of the container 110 (see FIG. 1). As shown in FIG. 1, the bracing arm 310 of the brace 340 is positioned approximately at the center of the container relative to the central vertical axis a. The brace 240 or bracing arm 310 can be positioned at the center or near to (e.g., within a threshold distance from) the center allowing for the wires 145A and 145B themselves to be positioned a certain distance from the center of the container 110 such as a cuvette. This allows the wires 145A and 145B to be in contact with the flow of the blood sample during mixing as the sample flows around the edge of the container 110, and avoids having the wires 145A and 145B in the center where there is less mixing relative to the edge of the container. This provides for better measurement of platelet function and aggregation. FIG. 1 illustrates how the wires 145A and 145B are positioned to one side of the container 110 rather than at the center. The electrode assembly 130 can be structured such that the wires 145A and 145B are positioned between, such as halfway between, the center of the container 110 to the edge of the container 110.

The electrode assembly 130 can also include an additional groove 270 that facilitates positioning of the wires 145A and 145B to an electrical contact. Thus, there is no need for contact pads attached to the substrate 135 to make the connection to an electrical contact, as is used in conventional designs, since the wires 145A and 145B themselves run along the grooves in the substrate 135 to the edges to an electrical contact such that the wires can be exposed to external connectors. For example, FIG. 2F shows the wires at the top portion on either side at 285A and 285B where the connection can be made to an external connector, and FIG. 2H shows an example of a design with contact pads 290A and 290B. Alternatively, the wires 145A and 145B of the electrode 130 could be attached to a conductive backing such as a copper plate or circuit board. The electrode assembly 130 can also include additional guides 250 that help align the container 110 with the electrode assembly 130, help align the two layers 210 and 220 of the electrode assembly 130 to each other, or help guide the wires 145A and 145B during assembly of the electrode assembly 130.

The wires 145A and 145B of the electrode 140 can be palladium-, silver-, or gold-coated copper or can be pure, uncoated palladium, silver, gold, or copper. Using palladium-coated copper, for example, can substantially reduce the price of manufacture of the electrode assembly (e.g., by a factor of 10). The wires can be attached to the electrode assembly 130 along the grooves 260 by glue, adhesive tape, heat staking, welding (e.g., ultrasonic welding), or any other suitable attachment method that does not damage the electrode 140. For example, with a single layer substrate, the wires might be glued or attached view another adhesive or ultrasonically welded to the single layer. These wires can be positioned within a groove of the single layer or otherwise positioned on the layer or embedded within the layer. Where the substrate has two layers, the wires can be secured between the layers, potentially within a groove formed by the two layers being united, or otherwise secured between the layers. Where the substrate has two layers, the wires 145A and 145B can be sealed or secured between the two layers 210 and 220, for example, within a groove formed by the two layers being united, or otherwise secured between the layers. In some embodiments, the wires may be secured between the layers by gluing, use of an adhesive tape, or heat staking. This securing between the layers prevents direct contact with the solution in the container 110.

The manufacturing and assembly process associated with the electrode assembly 130 is easier than the process required for conventional designs. The manufacturing and assembly of the electrode assembly 130 includes molding the piece of plastic that will form the substrate 135, threading the wires 145A and 145B within the grooves 260 of the substrate 135, and applying adhesive or other securing mechanism for the wires 145A and 145B. Conventional designs typically require multi-step, complicated process that involves securing contact pads to the device.

Figure 4:
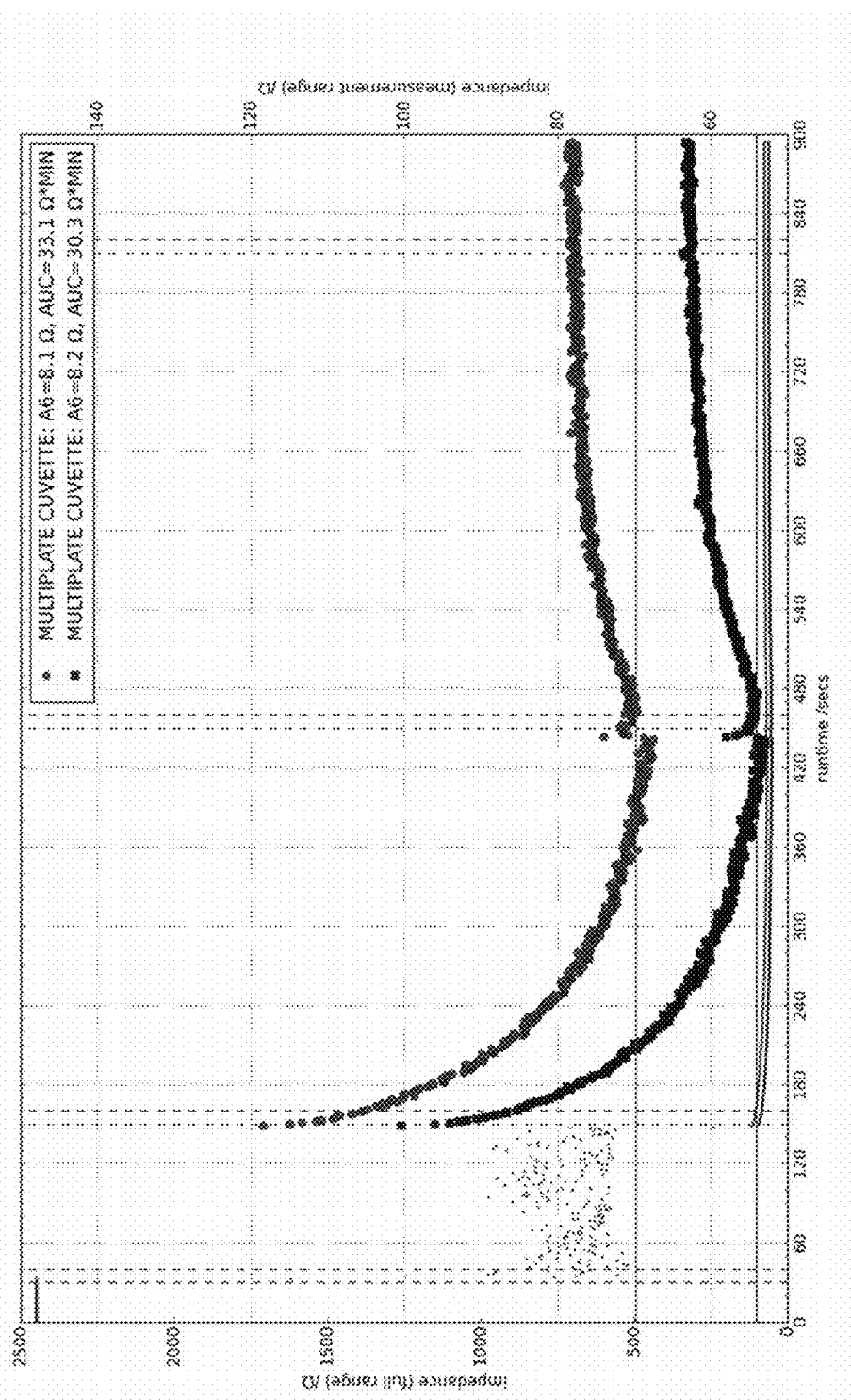
FIG. 4 illustrates impedance measurements of a conventional electrode assembly design, in accordance with an embodiment.

Further, conventional electrode assembly designs for measuring platelet function produce results with more noise, as shown in FIG. 4, than the electrode assembly 130 disclosed herein, as shown in FIGS. 5A, 5B, 5C, and 5D, where parameter "A6" represents amplitude at 6 minutes and parameter "AUC" represents area under the curve. FIGS. 5A, 5B, 5C, and 5D show impedance measurements of a sample using the electrode assembly 130 described herein with gold-coated wires (where one is cleaned and the other is uncleaned), silver-coated wires, gold-coated and silver-coated wires, and palladium-coated wires, respectively.

For each measurement in FIGS. 5, 5A, 5B, 5C, and 5D the figure shows both the preparation and measurement period in one graph. The x axis shows the run time (seconds). The primary y axis is broader and covers the impedance (ohms) range observed during the setup and measurement period. The secondary y axis shows the impedance range (ohms) observed during the measurement period. The period from T=0 to 450 seconds is used to set up the measurement. The vertical dashed lines at 30, 40 seconds and 150, 160 seconds represent the addition of saline and blood respectively. The dashed lines at 450, 460 seconds indicate when reagent was added and the start of the measurement period. The measurement period is 6 minutes and both parameters (A6 and AUC) are calculated are calculated at T=6 minutes. The final set of vertical dashed lines shows the end of the measurement. The graphs illustrate the results from a research system that mimics the measurement method that will ultimately be used with the electrode assembly in operation.

Figure 5A:
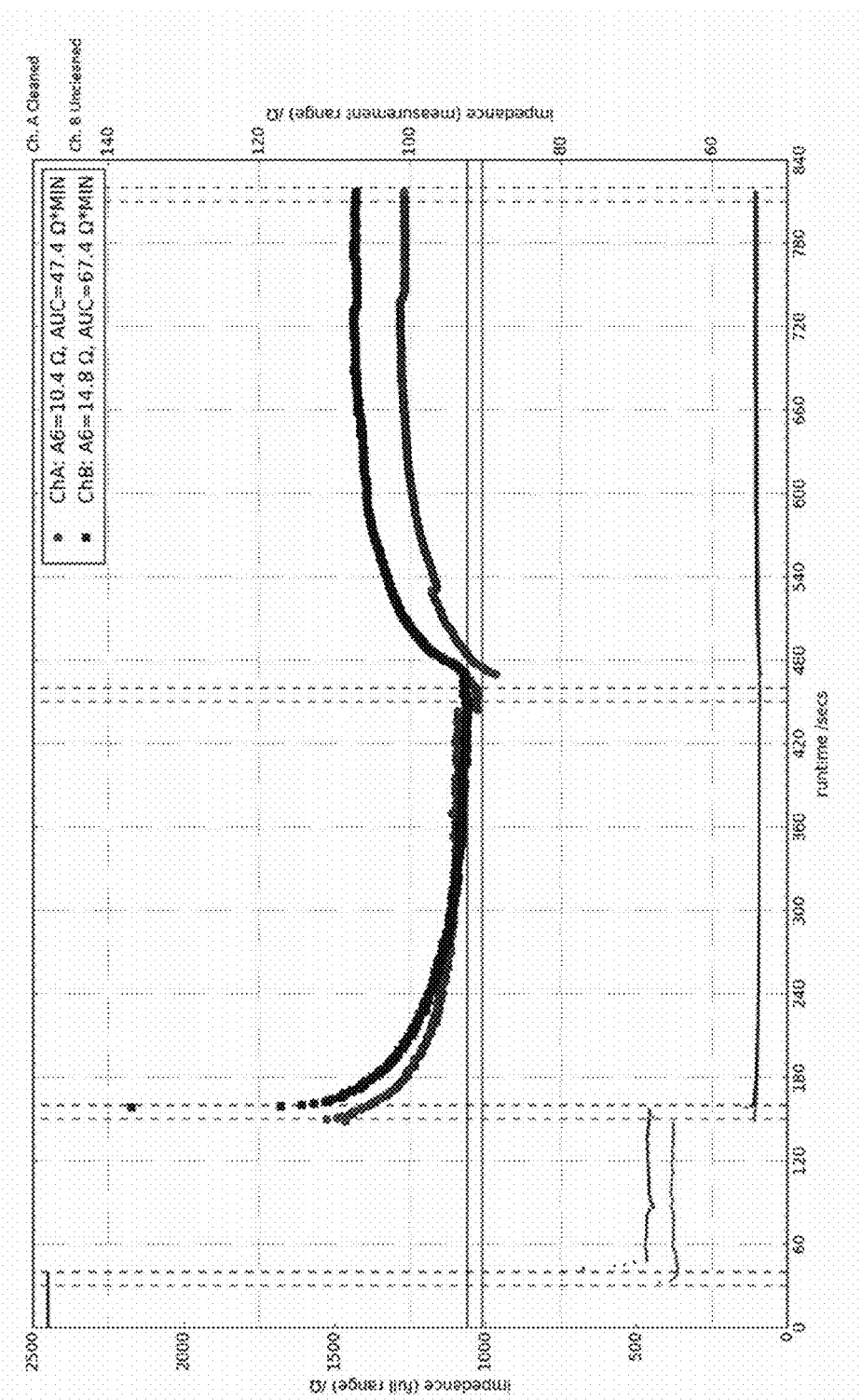
FIG. 5A illustrates impedance measurements of an electrode assembly using gold-coated wires, in accordance with an embodiment.
Figure 5B:
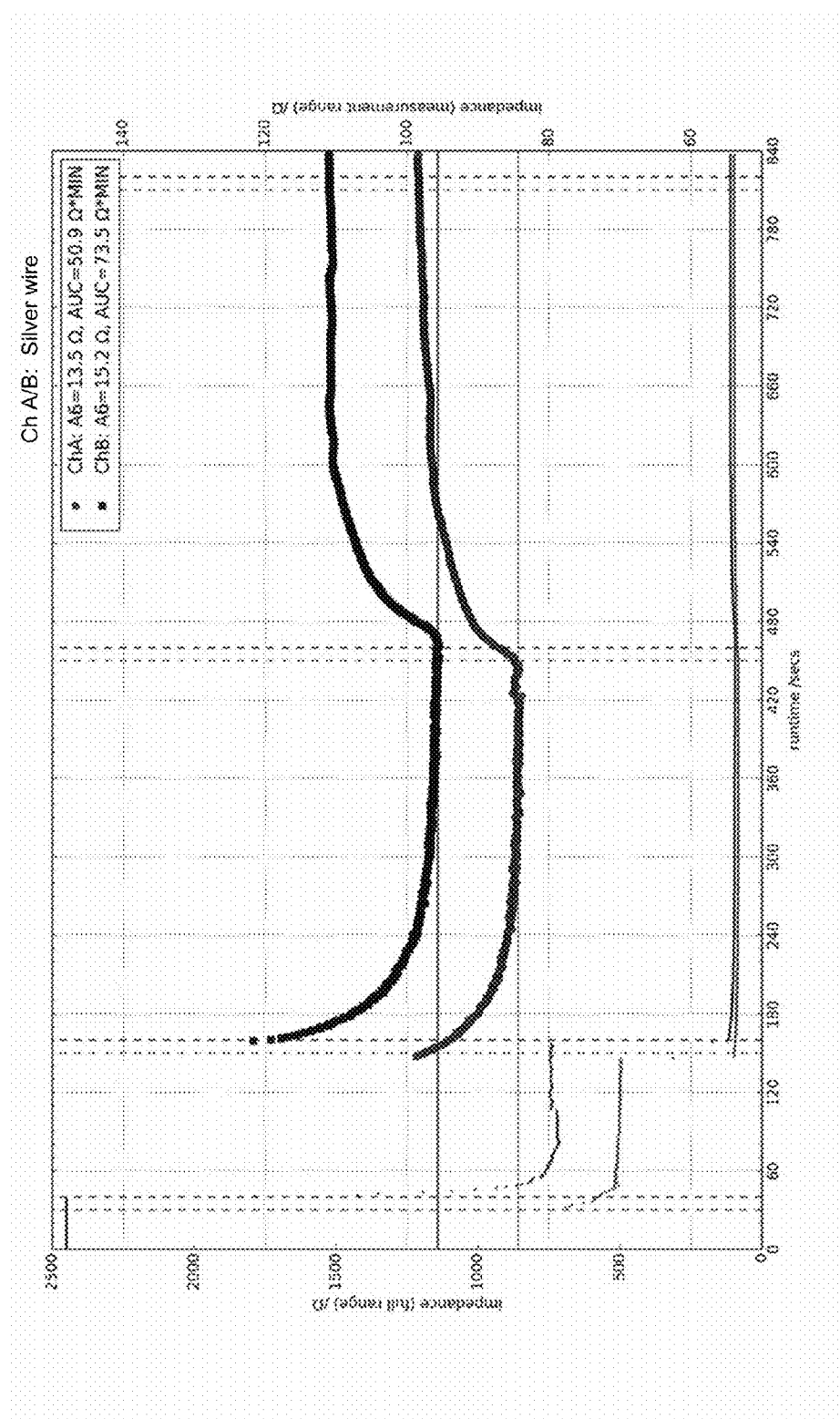
FIG. 5B illustrates impedance measurements of an electrode assembly using silver-coated wires, in accordance with an embodiment.
Figure 5C:
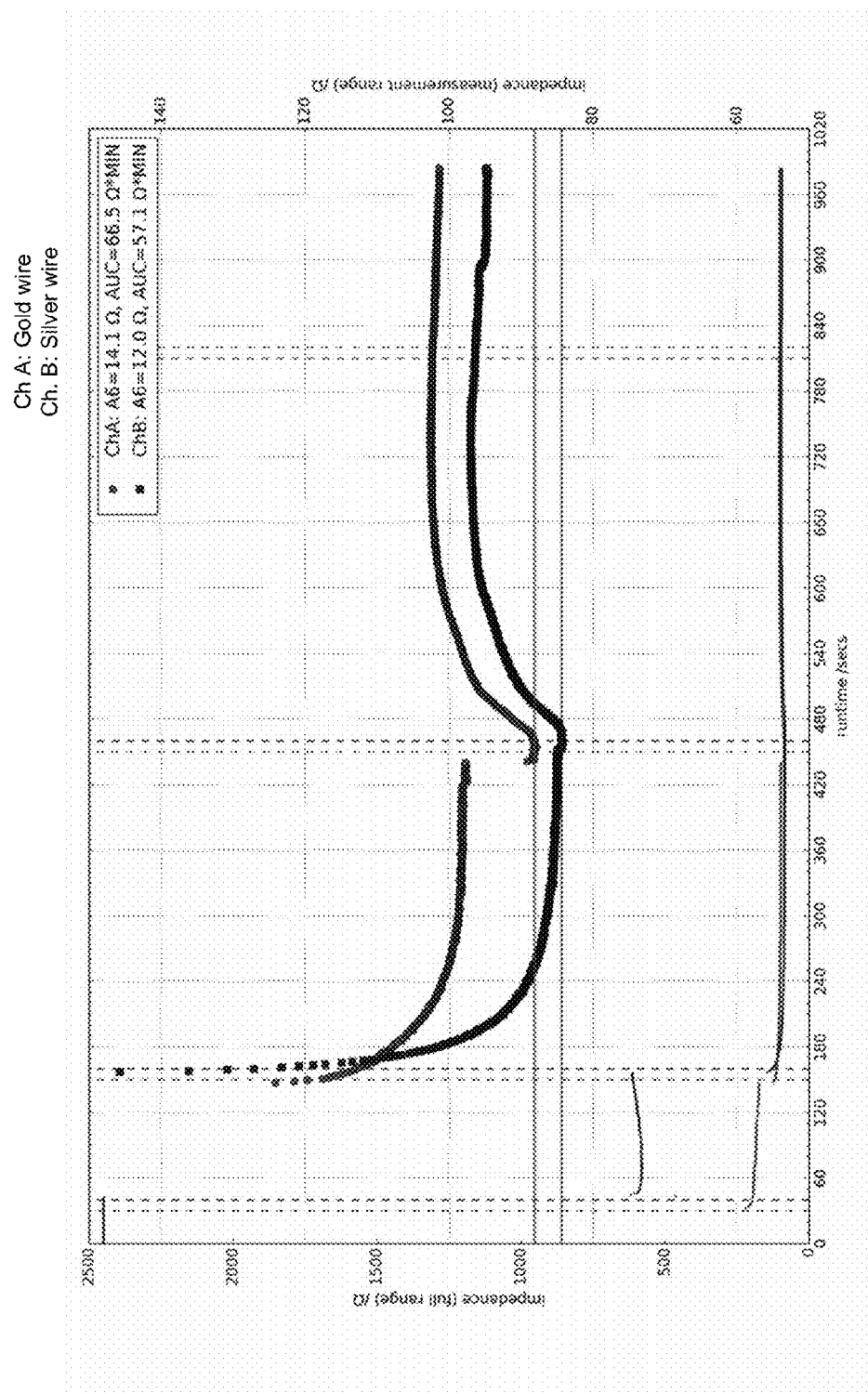
FIG. 5C illustrates impedance measurements of an electrode assembly using gold-coated and silver-coated wires, in accordance with an embodiment.
Figure 5D:
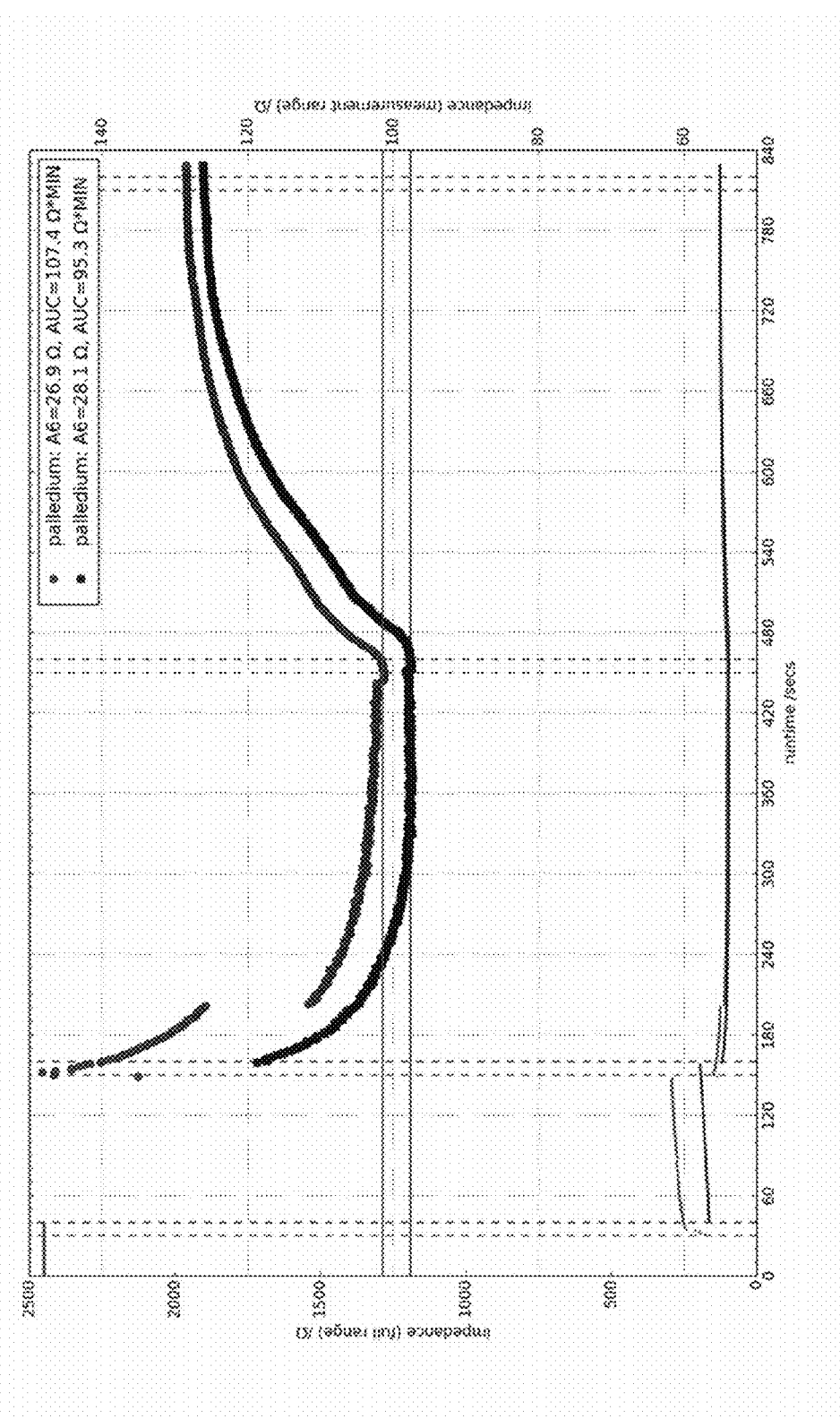
FIG. 5D illustrates impedance measurements of an electrode assembly using two palladium-coated wires, in accordance with an embodiment.

Two channels were run in parallel for each measurement such that testing could be conducted for two electrodes at once. The A6 and AUC values, as well as a descriptor for each channel, can be found in the legend (upper right hand corner). FIG. 4 shows two channels, channel A and B that were run with a conventional electrode assembly, and the graph shows some noise with this design. FIGS. 5A-5D show the electrode assembly 130 described throughout. Specifically, FIG. 5A shows channel A run with a cleaned electrode and channel B run with an uncleaned electrode, where both are gold electrodes. FIG. 5B shows channel A and B run with an electrode assembled using silver wire. FIG. 5C shows channel A run with an electrode assembled using gold wire and channel B run with an electrode assembled using silver wire. FIG. 5D shows channel A and B run with an electrode assembled using palladium wire. FIGS. 5B-D demonstrate that gold-coated and silver-coated copper wire generate a lower signal than palladium-coated wire.

SUMMARY

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. An electrode assembly to perform an impedance measurement in a blood sample, the electrode assembly comprising:
   an electrode comprising a plurality of wires; and
   a substrate comprising:
      a top portion that encloses the wires within the substrate, and
      a bottom portion comprising a brace, the brace having a top part and a bottom part separated by an opening that exposes a region of the wires such that, when the electrode assembly is placed in the blood sample, the exposed region of the wires contacts the blood sample, the brace securing the wires to the substrate on both sides of the opening at the top part of the brace and at the bottom part of the brace.

2. The electrode assembly of claim 1, wherein the substrate is composed of a rigid plastic.

3. The electrode assembly of claim 1, wherein the substrate comprises a first layer and a second layer that are mated to form the substrate, and wherein a region of the electrode is sealed between the first layer and the second layer of the substrate such that the sealed region does not contact the blood sample when the electrode assembly is submerged in the blood sample.

4. The electrode assembly of claim 3, wherein the first layer comprises a guide along which the wires of the electrode are secured to the substrate, the guide selected from a group consisting of: one or more grooves, one or more raised guides, and any combination thereof.

5. The electrode assembly of claim 1, wherein the top portion of the substrate has a section with a width greater than a width of the bottom portion, wherein the wires run parallel to each other and a fixed distance from each other vertically along the substrate, and wherein the wires run away from each other at the greater width section of the substrate.

6. The electrode assembly of claim 1, wherein the bottom portion of the substrate is off-center relative to the top portion of the substrate.

7. The electrode assembly of claim 1, wherein the top portion of the substrate is adapted to rest on or contact an edge of a container holding the blood sample so that the brace can be submerged in the blood sample, and wherein the bottom portion of the substrate is positioned such that the exposed region of the wires is off center within the container relative to a center vertical axis of the container, the wires being positioned perpendicular to a flow of the blood.

8. The electrode assembly of claim 1, wherein the exposed region of the wires comprises a region at which the wires exit and then reenter the substrate, the brace forming a C- or L-shaped section that fixes the wires in position such that the wires are parallel to each other.

9. The electrode assembly of claim 1, wherein the brace comprises:
   a bracing arm that extends substantially vertically away from a lowermost part of the bottom portion of the substrate;
   a securing base that extends substantially horizontally away from the bracing arm, the securing base securing an end of the plurality of wires of the electrode to the bottom part of the brace of the substrate.

10. An electrode assembly to perform an impedance measurement in a sample, the electrode assembly comprising:
    an electrode comprising a plurality of wires; and
    a substrate that is substantially rigid and that secures a position of the electrode, the substrate comprising a first layer and a second layer that enclose the wires within the substrate, the substrate further comprising a brace, the brace having a top part and a bottom part separated by an opening that exposes a region of the wires, the brace fixing the wires to the substrate on both sides of the opening at the top part of the brace and the bottom part of the brace such that, when the electrode assembly is placed in the sample, the exposed region of the wires contacts the sample.

11. The electrode assembly of claim 10, wherein the substrate is composed of a rigid plastic and the electrode is composed of palladium-coated copper.

12. The electrode assembly of claim 10, wherein the first layer and the second layer are combined to form the substrate, the electrode secured between the first layer and the second layer of the substrate such that the secured region does not contact the blood sample when the electrode assembly is submerged in the blood sample.

13. The electrode assembly of claim 12, wherein the substrate of the electrode assembly comprises a top portion and a bottom portion, the top portion exposes the electrode to external connectors and the bottom portion comprises the brace with the opening that exposes a portion of the electrode, a remaining portion of the electrode encompassed between the first layer and the second layer of the substrate.

14. The electrode assembly of claim 13, wherein the brace comprises:
    a bracing arm that extends substantially vertically away from a lowermost part of the bottom portion of the substrate;
    a securing base that extends substantially horizontally away from the bracing arm, the securing base securing an end of the plurality of wires of the electrode to the bottom part of the brace of the substrate.

15. The electrode assembly of claim 10, wherein the first layer comprises a guide along which the electrode is secured to the substrate, the guide selected from a group consisting of: one or more grooves, one or more raised guides, and any combination thereof.

16. The electrode assembly of claim 10, wherein the electrode assembly comprises a top portion and a bottom portion, the top portion of a width greater than a width of the bottom portion.

17. The electrode assembly of claim 16, wherein a center of the bottom portion of the electrode assembly and a center of the top portion of the electrode assembly are not aligned such that the bottom portion of the substrate is off-center relative to the top portion of the substrate.

18. A platelet impedance measurement system, the system comprising:
    a sample holder for holding a liquid sample; and
    an electrode assembly configured to couple with the sample holder to position a portion of the electrode assembly within the liquid sample in the sample holder, the electrode assembly comprising the electrode and a substantially rigid substrate that secures a position of the electrode, the substrate comprising a brace, the brace having a top part and a bottom part separated by an opening that exposes a region of the electrode, the brace fixing the electrode to the substrate on both sides of the opening at the top part of the brace and the bottom part of the brace such that, when the electrode assembly is placed in the liquid sample, the exposed region contacts the liquid sample.

19. The system of claim 18, the sample holder selected from a group consisting of: a cuvette, a test tube, or a flask.

20. The system of claim 18, further comprising a mixer selected from a group consisting of: a stir bar, rotor, or any combination thereof.

21. The system of claim 18, wherein the electrode assembly comprises one or more connectors at a top portion of the electrode assembly at which the electrode assembly couples with the sample holder.

22. The system of claim 18, wherein the substrate is composed of a rigid plastic.

23. The system of claim 18, wherein the substrate comprises a first layer and a second layer that are combined to form the substrate, and wherein the electrode is secured between the first layer and the second layer of the substrate.

24. The system of claim 23, wherein the electrode assembly comprises a top portion and a bottom portion, the bottom portion comprising the brace with the opening that exposes the region of the electrode, a remaining portion of the electrode encompassed between the first layer and the second layer of the substrate.

25. The system of claim 18, wherein the substrate comprises a one or more grooves along which the electrode is secured to the substrate.

26. The system of claim 18, wherein the electrode is composed of palladium-coated copper.

27. The system of claim 18, wherein the electrode assembly comprises a top portion and a bottom portion, the top portion of a width greater than a width of the bottom portion, and wherein a center of the bottom portion of the electrode assembly and a center of the top portion of the electrode assembly are not aligned.

* * * * *